United States Patent [19]

Leslie et al.

[11] Patent Number: 4,844,910
[45] Date of Patent: Jul. 4, 1989

[54] SPHEROIDS

[75] Inventors: Stewart T. Leslie, Cambridge; Sandra T. A. Malkowska, Landbeach; Joanne Marchant, St. Ives; Philip J. Neale, Harston, all of Great Britain

[73] Assignee: Euroceltique, S.A., Luxembourg

[21] Appl. No.: 122,747

[22] Filed: Nov. 19, 1987

[30] Foreign Application Priority Data

Dec. 2, 1986 [GB] United Kingdom ............... 8628728

[51] Int. Cl.$^4$ ................................................ A61K 9/16
[52] U.S. Cl. ...................................... 424/494; 424/461; 424/495; 424/496; 424/497; 424/498; 424/470
[58] Field of Search ............... 424/494, 495, 496, 461, 424/497, 498

[56] References Cited

U.S. PATENT DOCUMENTS

| 3,492,397 | 1/1970 | Peters et al. | 424/495 |
| 3,576,759 | 4/1971 | Powell et al. | 424/495 X |
| 4,587,118 | 5/1986 | Hsiao | 424/494 X |
| 4,748,023 | 5/1988 | Tamás et al. | 424/495 X |

FOREIGN PATENT DOCUMENTS

| 0122077 | 7/1984 | European Pat. Off. | 424/495 |
| 0130162 | 1/1985 | European Pat. Off. | 424/494 |
| 3306250 | 8/1984 | Fed. Rep. of Germany | 424/495 |
| 56-122311 | 9/1981 | Japan | 424/495 |

Primary Examiner—Thurman K. Page
Attorney, Agent, or Firm—Steinberg & Raskin

[57] ABSTRACT

A controlled release pharmaceutical composition comprising a plurality of film coated spheroids, the film coated spheroids comprising a 3-alkylxanthine, a non-water soluble spheronising agent and between 4% and 9% (by weight) water, wherein the in-vitro dissolution rate of the 3-alkylxanthine from the film coated spheroids, when measured by the USP Paddle Method at 100 rpm in 900 ml aqueous buffer (pH 6.5 at 37° C.) is between 7.5% and 25.0% (by wt) release after 1 hour, between 22.5% and 45.0% (by wt) release after 2 hours, between 40.0% and 60.0% (by wt) release after 3 hours, between 50.0% and 75.0% (by wt) release after 4 hours, between 70.0% and 92.5% (by wt) release after 6 hours, and between 80.0% and 100.0% (by wt) release after 8 hours. Preferably the water content is between 4% and 8%, especially between 4% and 7% (by wt) of the film coated spheroid formulation. The preferred 3-alkylxanthine is theophylline (anhydrous or hydrate), whilst the preferred spheronising agent is microcrystalline cellulose.

14 Claims, No Drawings

SPHEROIDS

The present invention relates to a controlled release pharmaceutical composition containing a 3-alkylxanthine.

It is one object of the present invention to provide a 3-alkylxanthine containing controlled release pharmaceutical composition having a narrow range of in-vitro dissolution rates over a wise pH range (pH 1.6 to 7.2). Other objects and advantages of the present composition will become apparent from the following detailed description thereof.

According to the present invention, there is provided a controlled release pharmaceutical composition comprising a plurality of film coated spheroids, the film coated spheroids comprising a 3-alkylxanthine, a non-water soluble spheronising agent and between 4% and 9% (by weight) water, wherein the in-vitro dissolution rate of the 3-alkylxanthine from the film coated spheroids, when measured by the USP Paddle Method at 100 rpm in 900 ml aqueous buffer (pH 6.5) at 37° C. is
between 7.5% and 25.0% (by wt) release after 1 hour,
between 22.5% and 45.0% (by wt) release after 2 hours,
between 40.0% and 60% (by wt) release after 3 hours,
between 50.0% and 75.0% (by wt) release after 4 hours,
between 70.0% and 92.5% (by wt) release after 6 hours, and
between 80.0% and 100% (by wt) release after 8 hours.

In the present specification "percent (by weight) water" refers to the water content of the spheroids as measured using a Karl Fischer titration method.

Preferably the water content of the film coated spheroids is between 4% and 8% (by weight), and the in vitro dissolution rate of the 3-alkylxanthine is between 8.0% and 22.5% (by wt) release after 1 hour, between 25% and 42.5% (by wt) release after 2 hours, between 42.5% and 60% (by wt) release after 3 hours, between 52.5% and 72.5% (by wt) release after 4 hours, between 72.5% and 92.5% (by wt) release after 6 hours and between 82.5% and 100% (by wt) release after 8 hours.

Most preferably, the water content is between 4% and 7% (by weight) and the in vitro dissolution rate is between 8.0% and 20% (by wt) release after 1 hour, between 25% and 40% (by wt) release after 2 hours, between 42.5% and 57.5% (by wt) release after 3 hours, between 55% and 70% (by wt) release after 4 hours, between 75.0% and 90.0% (by wt) release after 6 hours, and between 82.5% and 100% (by wt) release after 8 hours.

The term "spheroid" is known in the pharmaceutical art and means a spherical granule having a diameter of between 0.5 mm and 2.5 mm, especially between 0.5 mm and 2 mm.

The present inventors have surprisingly found that the water content of the present film coated spheroids has a dramatic effect on the in-vitro release rate of the active ingredient. When the water content of the film coated spheroids is below 4% (by wt), the release rate is too fast. When the water content of the film coated spheroids is above 9%, the release rate is too slow. For example, when two groups of film coated spheroids having identical formulations except for their water contents which were, respectively, 0.82% (by wt) and 10.26% (by wt), were subjected to in-vitro dissolution, it was found that the "0.82" formulation released, in-vitro, 60.2% (by wt) theophylline after 1 hour, 91.9% (by wt) after 2 hours, 95.7% (by wt) after 3 hours and 96.0% (by wt) after 4 hours, whilst the "10.26" formulation released, in-vitro, 7.1% (by wt) theophylline after 1 hour, 22.5% (by wt) after 2 hours, 38.1% (by wt) after 3 hours and 51.8% (by wt) after 4 hours.

It is a particular advantage of the present composition that the in-vitro dissolution rate is substantially independent of pH over a wide range (pH 1.6 to 7.2)

The present film coated spheroids contain a 3-alkylxanthine. The phrase "3-alkylxanthine" in the present specification incorporates
(i) Any xanthine substituted at the 3 nitrogen by an alkyl group, and
(ii) Any salt or derivative of such a 3-alkyl substituted xanthine.

Thus, the 3-alkylxanthine may be, for example, enprofylline or theobromine. Preferably, however, the 3-alkylxanthine is a 1,3-dimethylxanthine, such as acepifylline, bamifylline, bufylline, diprophylline, etamiphylline, etofylline, proxyphylline or theophylline. Of these 1,3-dimethyl xanthines, theophylline (anhydrous or hydrate) or a salt or derivative of theophylline, such as aminophylline, choline theophyllinate, theophylline monoethanolamine, theophylline sodium glycinate or theophylline calcium salicylate is particularly preferred. Theophylline (anhydrous or hydrate) is the most preferred.

Preferred doses of the 3-alkylxanthines in a unit dose of the present composition are as follows:

| Acepifylline | 125–1000 mg |
| Aminophylline | 50–450 mg |
| Bamifylline HCl | 150–600 mg |
| Bufylline | 30–120 mg |
| Choline Theophyllinate | 50–400 mg |
| Diprophylline | 50–400 mg |
| Enprofylline | 50–600 mg |
| Etamiphylline camsylate | 50–600 mg |
| Etofylline | 100–600 mg |
| Proxyphylline | 100–600 mg |
| Theobromine | 50–600 mg |
| Theophylline | 50–400 mg |
| Theophylline Monoethanolamine | 50–400 mg |
| Theophylline Na Glycinate | 50–600 mg |

The concentration of 3-alkylxanthine in the present film coated spheroids will depend, amongst other factors, on the amount of xanthine to be administered and the total weight of film coated spheroids to be administered. In the case of theophylline, the film coated spheroids preferably contain between 40% and 75% (by wt), especially between 45% and 70% (by wt), of the active ingredient.

The spheronising agent may be any pharmaceutically acceptable material that, together with the active ingredient, can be spheronised to form spheroids. Microcrystalline cellulose is preferred.

A suitable microcrystalline cellulose is, for example, the material sold as Avicel PH 101 (Trade Mark, FMC Corporation). According to one preferred embodiment of the present composition, the film coated spheroids contain between 20% and 50% (by wt), especially between 25% and 45% (by wt), of the spheronising agent, especially microcrystalline cellulose.

In addition to the 3-alkylxanthine, spheronising agent and water, the present spheroids may also contain a binder. Suitable binders, such as low viscosity, water soluble polymers, will be well known to those skilled in the pharmaceutical art. However, water soluble hydroxy lower alkyl celluloses, such as hydroxy propyl cellulose, are preferred.

The present spheroids are film coated with a material that permits release of the 3-alkylxanthine at a controlled rate in an aqueous medium. The film coat is chosen so as to achieve, in combination with the spheroids' other ingredients, the in-vitro release rate outlined above (between 7.5% and 25.0% (by wt) release after 1 hour, etc.).

The film coat will generally include a water insoluble material such as
(a) a wax, either alone or in admixture with a fatty alcohol,
(b) shellac or zein,
(c) a water insoluble cellulose, especially ethyl cellulose,
(d) a polymethacrylate, especially Eudragit (Trade Mark).

Preferably, the film coat comprise a mixture of the water insoluble material and a water soluble material. The ratio of water insoluble to water soluble material is determined by, amongst other factors, the release rate required and the solubility characteristics of the materials selected.

The water soluble material may be, for example, polyvinylpyrrolidone or, which is preferred, a water soluble cellulose, especially hydroxypropylmethyl cellulose.

Suitable combinations of water insoluble and water soluble materials for the film coat include shellac and polyvinylpyrrolidone or, which is preferred, ethyl cellulose and hydroxypropylmethyl cellulose.

A unit dose of the present pharmaceutical composition may consist of, for example, a capsule, sachet or cachet containing a predetermined quantity of film coated spheroids. In the case of a capsule or cachet, the dosage form may be administered directly via the oral route. In the case of a capsule, sachet or cachet, the film coated spheroids may be sprinkled onto food which is then taken as part of a meal.

The present controlled release pharmaceutical composition may be prepared, in a second aspect of the present invention, by
(a) granulating a mixture comprising a 3-alkylxanthine, a non-water soluble spheronising agent and water,
(b) extruding the granulated mixture to give an extrudate,
(c) spheronising the extrudate until spheroids are formed,
(d) drying the spheroids, and
(e) coating the spheroids with a film coat that permits release of the 3-alkylxanthine at a controlled rate in an aqueous medium, to give film coated spheroids, wherein the spheroids are dried in step (d) above to such an extent that the film coated spheroids contain between 4% and 9% (by weight) water and the in-vitro dissolution rate of the 3-alkylxanthine from the film coated spheroids, when measured by the USP Paddle Method at 100 rpm in 900 ml aqueous buffer (pH 6.5) at 37° C. is
between 7.5% and 25.0% (by wt) release after 1 hour,
between 22.5% and 45.0% (by wt) release after 2 hours,
between 40.0% and 60.0% (by wt) release after 3 hours,
between 50.0% and 75.0% (by wt) release after 4 hours,
between 70.0% and 92.5% (by wt) release after 6 hours, and
between 80.0% and 100% (by wt) release after 8 hours.

Preferably, after drying, in step (d) above, the spheroids are sieved to give spheroids having a predetermined particle size range.

The present composition and process will now be described by way of Example only.

DETERMINATION OF WATER CONTENT BY THE KARL FISCHER METHOD

1. A Karl Fischer Autotitration unit (Baird and Tatlock) was set up according to the manufacturer's instructions.
2. A sample volume of Karl Fischer reagent (Fisons) was standardised.
3. A predetermined quantity of spheroids was ground to a fine powder in a mortar and pestle.
4. Approximately 0.5 g of the powdered spheroids were weighed into the sample vessel.
5. The Karl Fischer reagent was neutralised in the reaction vessel and then the sample was added. The mixture was stirred for 3 minutes.
6. The sample vessel was reweighed in order to determine the weight of sample used.
7. A Karl Fischer titration was then carried out in the reaction vessel, the amount of titrant added being noted. The test was carried out in duplicate.

EXAMPLE 1

Spheroid Formation

Anhydrous theophylline (BP, 60.61 parts by wt), microcrystalline cellulose (Avicel PH 101, Trade Mark, 37.39 parts by wt) and hydroxypropyl cellulose (Klucel GF, Trade mark, 2.0 parts by wt) were dry mixed. Water (550 parts by weight) was added to the mixture until a densely granulated mass was obtained. The granulated mass was passed through a 1 mm cylinder on an extruder to give a uniform, free flowing extrudate. The extrudate was then spheronised.

The wet spheroids were dried until they had a water content (as measured by the Karl Fischer method) of 6.49 wt % (of the total spheroid weight). Finally, the spheroids were sieved to give a particle size range between 1.0 and 1.4 mm.

Film Coating

A film coat containing the following ingredients, in a solvent system consist of methanol (60% v/v) in dichloromethane was employed,

|  | % w/v |
| --- | --- |
| Ethyl cellulose NF (N10, Trade Mark) | 3.5 |
| Hydroxypropylmethyl cellulose EP (Methocel E15, Trade Mark) | 1.5 |
| Propylene glycol BP | 0.5 |
| Opaspray K-1-7000B (Trade Mark) | 3.0 |

The dried spheroids were film coated with the above formulation. The dried film coat corresponded to about 6.7% (w/w) of the total, film coated spheroid weight. The film coated spheroids had a water content (by Karl Fischer) of 6.2 wt % (of the total, film coated spheroids weight).

EXAMPLE 2

The procedure of Example 1 was followed except that the spheroids were dried until they had a water content of 6.8 wt % (of the total spheroid weight). The film coated spheroids had a water content of 5.6 wt % (of the total, film coated spheroid weight).

EXAMPLE 3

The procedure of Example 1 was followed except that the spheroids were dried until they had a water content of 7.3 wt % (of the total spheroid weight). The film coated spheroids had a water content of 6.4 wt % (of the total, film coated spheroid weight).

EXAMPLE 4

The procedure of Example 1 was followed except that the spheroids were dried until they had a water content of 6.7 wt % (of the total spheroid weight). The film coated spheroids had a water content of 5.8 wt % (of the total, film coated spheroid weight).

EXAMPLE 5

The procedure of Example 1 was followed except that the spheroids were dried until they had a water content of 6.9 wt % (of the total spheroid weight). The film coated spheroids had a water content of 5.95 wt % (of the total, film coated spheroid weight).

COMPARATIVE EXAMPLE

The procedure of Example 1 was followed except that the spheroids were dried until they had a water content of 12.0 wt % (of the total spheroid weight). The film coated spheroids had a water content of 10.3 wt % (of the total, film coated spheroid weight).

COMPARATIVE EXAMPLE

The procedure of Example 1 was followed except that the spheroids were dried until they had a water content of 0.5 wt % (of the total spheroid weight). The film coated spheroids had a water content of 0.8 wt % (of the total, film coated spheroid weight).

EXAMPLE 6

Spheroid Formation

Anhydrous theophylline (BP, 50 parts by wt), microcrystalline cellulose (Avicel PH101, Trade Mark, 46 parts by wt) and hydroxyethylcellulose (Natrosol 250L, 4 parts by wt) were dry mixed. Water (600 parts by wt) was added to the mixture until a densely granulated mass was obtained. The granulated mass was passed through a 1 mm cylinder on an extruder to give a uniform, free flowing extrudate. The extrudate was then spheronised.

The wet spheroids were dried. Finally the spheroids were sieved to give a particle size range between 1.0 and 1.4 mm.

Film Coating

A film coat containing the following ingredients, in a solvent system consisting of methanol (60% v/v) in dichloromethane was employed,

|  | % w/v |
|---|---|
| Ethyl cellulose NF (N10, Trade Mark) | 3.5 |
| Hydroxypropylmethyl cellulose EP (Methocel E15, Trade Mark) | 1.5 |
| Propylene Glycol BP | 0.5 |
| Opaspray K-1-7000B (Trade Mark) | 3.0 |

The dried spheroids were film coated with the above formulation. The dried film coat corresponded to about 17% (w/w) of the total, film coated spheroid weight. The film coated spheroids had a water content (by Karl Fischer) of 4.4 wt % (of the total, film coated spheroids weight)).

DISSOLUTION METHODS

A. Materials

1. Dissolution Apparatus

USP Paddle Dissolution apparatus fitted with a peristaltic pump and a UV spectrophotometer. The spectrophotometer had 1 mm pathlength flow cells.

2. Reagents

Theophylline anhydrous (BP of known purity) Sodium Hydroxide (AR) Potassium dihydrogen orthophosphate (AR) Distilled, deionised water 3. pH USP Buffer Potassium dihydrogen orthophosphate (6.805 g) and sodium hydroxide (0.56 g) was dissolved in distilled water (1 liter) for each liter of buffer required.

The pH of the solution was adjusted, if necessary, to pH 6.5. Prior to use, the buffer solution was purged with helium for at least 30 minutes.

Methods

Medium: USP Buffer, pH 6.5, deaerated
Volume: 900 ml
Temperature: 37° C.±0.5° C.
Paddle Speed: 100 rpm
Sampling Time: 1 hour intervals
Sampling Period: until at least 90 wt % theophylline released
Pump Speed: 15 ml/minute
Detection: UV absorbance at 244 nm
Pathlength: 1 mm

TABLE 1

Dissolution Results (mean of 5 samples)
(% Theophylline Released)

| Example | Water Content of Film Coated Spheroids (wt %) | 1 hr | 2 hr | 3 hr | 4 hr | 5 hr | 6 hr | 7 hr | 8 hr | 10 h |
|---|---|---|---|---|---|---|---|---|---|---|
| 1 | 6.2 | 13.9 | 33.7 | 50.2 | 64.0 | 75.1 | 83.7 | 90.2 | 95.5 | 100 |
| 2 | 5.6 | 13.5 | 34.1 | 51.1 | 64.8 | 75.8 | 84.1 | 90.7 | 95.4 | 100 |
| 3 | 6.4 | 17.3 | 36.2 | 52.6 | 65.2 | 75.6 | 84.3 | 89.9 | 94.5 | 99.4 |
| 4 | 5.8 | 13.9 | 33.7 | 50.2 | 63.5 | 74.5 | 83.0 | 89.7 | 94.4 | 99.4 |
| 5 | 5.95 | 12.0 | 30.0 | 45.3 | 57.9 | 68.5 | 76.6 | 83.0 | 87.9 | 92.6 |
| 6 | 4.4 | 10.4 | 30.6 | 47.9 | 62.0 | 73.1 | 82.5 | 90.2 | 94.7 | 100.4 |
| Comparative | 10.3 | 7.1 | 22.5 | 38.1 | 51.8 | 64.0 | 73.8 | 82.0 | 88.1 | 95.6 |

TABLE 1-continued

| Example | Water Content of Film Coated Spheroids (wt %) | 1 hr | 2 hr | 3 hr | 4 hr | 5 hr | 6 hr | 7 hr | 8 hr | 10 h |
|---|---|---|---|---|---|---|---|---|---|---|
| Comparative | 0.8 | 60.2 | 91.9 | 95.7 | 96.0 | — | — | — | — | — |

Dissolution Results (mean of 5 samples) (% Theophylline Released)

Film coated spheroids prepared according to the methods of Examples 1 to 6 and the Comparative Examples were subjected to the above in-vitro dissolution test. The results obtained are set out in Table 1.

B. The dissolution method was as described in Method A except that the buffer was pH 1.6 USP Buffer.

pH 1.6 USP Buffer

Potassium chloride (3.7275 g) and hydrochloric acid (1M, 32.4 ml) was dissolved in distilled water for each liter of buffer required. The pH of the solution was adjusted, if necessary, to pH 1.6. Prior to use, the buffer solution was purged with helium for at least 30 minutes.

Film coated spheroids prepared according to Example 5 were subjected to the in-vitro dissolution test (pH 1.6). The results (mean of 5 experiments) obtained are set out in Table 2.

TABLE 2

Dissolution of Film coated Spheroids (Water Content 5.95 wt %) in USP Buffer, pH 1.6

| Time (hr) | % Theophylline Released (by wt) |
|---|---|
| 1.0 | 13.8 |
| 2.0 | 34.5 |
| 3.0 | 51.7 |
| 4.0 | 65.3 |
| 5.0 | 75.9 |
| 6.0 | 83.8 |
| 7.0 | 89.6 |
| 8.0 | 93.0 |
| 10.0 | 95.8 |

CLINICAL STUDIES

A. A 12 volunteer study was carried out to compare the steady state pharmacokinetics of
(i) Theophylline spheroids (200 mg theophylline) prepared as described in Example 5, and
(ii) A sustained release theophylline tablet (UNIPHYLLIN CONTINUS tablet containing 200 mg theophylline).

Method

12 Healthy male volunteers were studied on two separate occasions. During each study period of 6 days, the subjects received either a UNIPHYLLIN CONTINUS tablet containing 200 mg of theophylline b.d. or theophylline spheroids (Example 5, 200 mg of theophylline) b.d. for 5 days, with a single dose of either tablet or spheroids being administered on the morning of day 6.

Blood samples were collected over 24 hours following this last dose and the plasma obtained was analysed for theophylline.

Plasma theophylline concentrations are given in Table 3.

TABLE 3

Plasma Theophylline Concentration (mcg ml$^{-1}$)

| Time (hr) | UNIPHYLLIN CONTINUS TABLETS | THEOPHYLLINE SPHEROIDS |
|---|---|---|
| 0 | 4.0 | 3.4 |
| 4 | 4.1 | 4.1 |
| 5 | 4.3 | 4.6 |
| 6 | 4.2 | 4.2 |
| 7 | 4.3 | 4.0 |
| 8 | 4.1 | 3.9 |
| 10 | 3.7 | 4.2 |
| 12 | 3.5 | 3.0 |
| 24 | 1.2 | 0.9 |

Theophylline spheroids (Example 5) were found, on the basis of this study, to be bioequivalent to the UNIPHYLLIN CONTINUS tablet.

B. A volunteer, single dose, crossover study was carried out to compare the pharmacokinetic properties of
(i) Theophylline spheroids (200 mg theophylline) prepared as described in Example 6, and
(ii) A sustained release theophylline tablet (UNIPHYLLIN CONTINUS tablet containing 400 mg theophylline).

Results are given in Table 4.

TABLE 4

Plasma Theophylline Concentration (mcg ml$^{-1}$)

| Time (hr) | UNIPHYLLIN CONTINUS TABLETS | THEOPHYLLINE SPHEROIDS |
|---|---|---|
| 0 | 0 | 0.1 |
| 1 | 1.3 | 0.6 |
| 2 | 2.7 | 1.8 |
| 3 | 3.8 | 2.2 |
| 4 | 4.5 | 3.2 |
| 6 | 5.2 | 4.0 |
| 8 | 5.4 | 4.6 |
| 10 | 5.5 | 2.9 |
| 12 | 5.0 | 2.3 |
| 24 | 1.4 | 0.9 |

This study showed that the theophylline spheroid formulation had the same bioavailability as a UNIPHYLLIN CONTINUS tablet.

What I claim is:

1. A controlled release pharmaceutical composition comprising a plurality of film coated spheroids, the film coated spheroids comprising a 3-alkylxanthine the alkyl group of which is up to three carbon atoms, microcrystalline cellulose as a non-water soluble spheronising agent and between 4% and .9% (by weight) water, wherein the in-vitro dissolution rate of the 3-alkylxanthine from the film coated spheroids, when measured by the USP Paddle Method at 100 rpm in 900 ml aqueous buffer (pH 6.5) at 37° C. is
between 7.5% and 25.0% (by wt) release after 1 hour,
between 22.5% and 45.0% (by wt) release after 2 hours,
between 40.0% and 60.0% (by wt) release after 3 hours,
between 50.0% and 75.0% (by wt) release after 4 hours,
between 70.0% and 92.5% (by wt) release after 6 hours, and
between 80.0% and 100.0% (by wt) release after 8 hours.

2. A composition according to claim 1 wherein the film coated spheroids contain between 4% and 8% (by weight) water and the in vitro dissolution rate of the 3-alkylxanthine is between 8.0% and 22.5% (by wt) release after 1 hour,
between 25% and 42.5% (by wt) release after 2 hours,
between 42.5% and 60% (by wt) release after 3 hours,
between 52.5% and 72.5% (by wt) release after 4 hours,
between 72.5% and 92.5% (by wt) release after 6 hours, and
between 82.5% and 100% (by wt) release after 8 hours.

3. A composition according to claim 2 wherein the film coated spheroids contain between 4% and 7% (by weight) water and the in vitro dissolution rate of the 3-alkylxanthine is between 8% and 20% (by wt) release after 1 hour,
between 25% and 40% (by wt) release after 2 hours,
between 42.5% and 57.5% (by wt) release after 3 hours,
between 55% and 70% (by wt) release after 4 hours,
between 75% and 90% (by wt) release after 6 hours, and
between 82.5% and 100% (by wt) release after 8 hours.

4. A composition according to claim 1 wherein the 3-alkylxanthine comprises a 1,3-dimethylxanthine or a salt or derivative of a 1,3-dimethylxanthine.

5. A composition according to claim 4 wherein the 3-alkylxanthine comprises acepifylline, bamifylline, bufylline, diprophylline, etamiphylline, etofylline, proxyphylline or theophylline.

6. A composition according to claim 4 wherein the 3-alkylxanthine comprises theophylline, aminophylline, choline theophyllinate, theophylline monoethanolamine, theophylline sodium glycinate or theophylline calcium salicylate.

7. A composition according to claim 6 wherein the 3-alkylxanthine comprises theophylline.

8. A composition according to claim 7 wherein the film coated spheroids comprise between 40% and 75% (by weight) theophylline.

9. A composition according to claim 8 wherein the film coated spheroids comprise between 45% and 70% (by weight) theophylline.

10. A composition according to claim 1 wherein the film coated spheroids comprise between 20% and 50%, (by weight) of the spheronising agent.

11. A composition according to claim 10 wherein the film coated spheroids comprise between 25% and 45% (by weight) of the spheronising agent.

12. A composition according to claim 1 wherein the film coat comprises ethyl cellulose and hydroxypropylmethyl cellulose.

13. A process for the preparation of a controlled release pharmaceutical composition comprising a plurality of film coated spheroids comprising (a) granulating a mixture comprising a 3-alkylxanthine, the alkyl group of which is up to three carbon atoms microcrystalline cellulose as non-water soluble spheronising agent and water to form a granulated mixture,
(b) extruding the thus formed granulated mixture to give an extrudate,
(c) spheronising the extrudate until spheroids are formed,
(d) drying the spheroids to a water content of between 4% and 9% (by weight), and coating the spheroids with a film coat that permits release of the 3-alkylxanthine at a controlled rate in an aqueous medium, to give film coated spheroids containing between .4% and 9% (by weight) water and the in-vitro underlying dissolution rate of the 3-alkylxanthine from the film coated spheroids, when measured by the USP Paddle Method at 100 rpm on 900 ml aqueous buffer (pH 6.5) at 37° C. is between 7.5% and 25.0% (by wt) release after 1 hour,
between 22.5% and 45.0% (by wt) release after 2 hours,
between 40.0% and 60.0% (by wt) release after 3 hours,
between 50.0% and 75.0% (by wt) release after 4 hours,
between 70.0% and 92.5% (by wt) release after 6 hours, and
between 80.0% and 100% (by wt) release after 8 hours.

14. A process according to claim 13 wherein, after the spheroids are dried and before the spheroids are film coated, the spheroids are sieved to give spheroids having a predetermined particle size range.

* * * * *